United States Patent [19]
Adell

[11] Patent Number: 5,346,395
[45] Date of Patent: Sep. 13, 1994

[54] DENTAL ARCH BITE REGISTRATION DEVICE

[75] Inventor: Loren S. Adell, 200 Adell Blvd., Sunnyvale, Tex. 75182

[73] Assignees: Loren S. Adell; Michael Adell, Sunnyvale, Tex.

[21] Appl. No.: 47,783

[22] Filed: Apr. 15, 1993

[51] Int. Cl.$^5$ ............................................. A61C 9/00
[52] U.S. Cl. ..................................... 433/71; 433/37; 433/48; 433/214
[58] Field of Search .................. 433/6, 37, 48, 71, 214

[56] References Cited

U.S. PATENT DOCUMENTS

| | | | |
|---|---|---|---|
| 603,803 | 5/1898 | White | 433/37 |
| 1,303,545 | 5/1919 | Downie | 433/71 |
| 1,778,293 | 10/1930 | Galasso | 433/37 |
| 2,183,624 | 12/1939 | Schwartz | 433/71 |
| 4,624,640 | 11/1986 | Tesini | 433/71 |
| 4,776,792 | 10/1988 | Wagner et al. | 433/71 |
| 4,867,680 | 9/1989 | Hare et al. | 433/71 X |
| 5,011,407 | 4/1991 | Pelerin | 433/48 |
| 5,108,286 | 4/1992 | Freedman et al. | 433/37 |

*Primary Examiner*—Gene Mancene
*Assistant Examiner*—Nicholas D. Lucchesi
*Attorney, Agent, or Firm*—George L. Boller

[57] ABSTRACT

Multi-laminar bite registration devices are fabricated from ethylene vinyl acetate. Injection molding is used to bond one lamina to another without the use of separate adhesive. The lamina have different durometers. In one embodiment, two relatively low durometer lamina are injection molded onto opposite surfaces of a relatively higher durometer lamina. In another, a relatively lower durometer lamina is injection molded onto a relatively higher durometer lamina.

20 Claims, 6 Drawing Sheets

DENTAL ARCH BITE REGISTRATION DEVICE

FIELD OF THE INVENTION

This invention relates to dentistry and in particular to a bite registration device.

BACKGROUND OF THE INVENTION

A bite registration device is used to obtain a model of the registration of an individual's dental arches for laboratory use in fabricating an appliance for treating the individual. Historically, bite registrations have been obtained by using wax. The wax is shaped to conform to the general arch shape, and then placed intra-orally between the individual's upper and lower dental arches. The individual is instructed to bite into the wax. The bite creates arch impressions in the wax that provide the registration of one arch to the other. The impression-containing wax is later used in conjunction with other dental equipment, such as dental casts and an articulator, to fabricate an appliance that will have the proper fit for the individual's bite.

While wax has enjoyed long-standing usage for bite registration, it is not without problems. It may warp, bend, and/or become brittle, depending on how it is handled, stored, and used. If these, or other similar, occurrences happen to the wax before it has served its intended purpose, treatment of the individual may be compromised or complicated.

It has also been proposed to obtain bite registration concurrent with obtaining full dental arch impressions. An example of a device that is used for that purpose is described in U.S. Pat. No. 3,302,289. One potential disadvantage of simultaneously obtaining full dental arch impressions and bite registration in a single device is that subsequent use of the resulting model may be compromised. It is believed that fabrication of an appliance for an individual is facilitated, and the appliance is apt to have a better fit, if bite registration is obtained separately from full dental arch impressions.

The present invention relates to a new and unique bite registration device that offers significant benefit over prior devices, especially wax bite registrations. The bite registration device of the present invention retains an accurate registration that remains dimensionally stable under normal usage, yet possesses a certain limited resilient flexibility. This flexibility is beneficial because it allows the device to be peeled from an arch to which it may adhere after having been bitten on by an individual, and also to be readily peeled from a dental cast. While care must of course be prudently exercised in handling and using the device, it is believed that the device is more tolerant to handling than prior bite registration devices.

The device of the present invention has the further advantage that its occlusal wall can be made relatively thin. This is important because it allows the individual to more closely approach full closure of the arches when biting into the device. The closer that the bite is to full closure, the better the result obtained.

A further aspect of the invention relates to the use of polymer and/or copolymer materials in the fabrication of the bite registration device. While certain principles of the invention do not depend specifically on the materials used, preferred materials include various durometers of ethylene vinyl acetate. These preferred materials provide important benefits. One important benefit is that a bite registration device according to the invention can be made by injection molding. It is hygenically manufactured and hermetically sealed until ready to be used by a dentist or orthodontist. For use, it is heated to slightly soften the material, and then placed between dental arches and bitten on by the individual. It is allowed to cool to stabilize the registration, and thereafter removed from the mouth. It then becomes available for use as needed in the course of procedures for fabricating an appliance, or other device, for the individual.

The device possesses certain constructional features that have significance in injection molding processes for fabricating the device. One constructional feature involves a series of small holes in certain lamina of the device. These holes are the result of using stand-off pins to hold another lamina in the mold cavity of an injection mold while the injected material is being forced into the cavity onto the held lamina. This aspect of using stand-off pins is described in more detail in my co-pending patent application relating to Dental Arch Appliances, Ser. No. 07/801,673, filed Dec. 2, 1991. Another constructional feature relates to the inclusion of V-shaped notches in the held lamina. These notches have been found to improve the flow of the material being molded onto the held lamina such that the proper lamination result is obtained.

While the use of ethylene vinyl acetate is not broadly new in intra-oral devices, it appears that its use has not heretofore been proposed for a bite registration device. Perhaps this is because of a desire that a bite registration device have a relatively thin occlusal wall. According to certain principles of the invention, a bite registration device having a relatively thin occlusal wall, not greater than 0.100 inch thick, is provided by multi-laminar ethylene vinyl acetate wherein one lamina has a durometer different from that of another. While the thickness of an occlusal wall cannot be so small that a bite results in excessive bite-through, a minor amount of bite-through that does not destroy the general integrity of the registration is not considered objectionable in most instances. In one specific embodiment of device to be described herein, one lamina has a durometer and a thickness that provide a majority of the resistance to bite-through, but in doing so takes an impression of only the cusps and tips of teeth of the arch impressed into it while Ether, softer lamina takes a deeper impression of teeth of the other arch. This specific embodiment is entirely acceptable even though it has such a relatively thin occlusal wall. Another specific embodiment of device to be described herein comprises two relatively softer lamina on opposite sides of a relatively harder intermediate lamina. This other embodiment provides deeper arch impressions than the first embodiment, but it has an occlusal wall whose thickness is greater. The first embodiment may be preferred by orthodontists and dentists in some instances while the second may be preferred in others.

The foregoing features, advantages, and benefits of the invention, along with additional ones, will be seen in the ensuing description and claims which are accompanied by drawings. The drawings disclose a presently preferred embodiment of the invention according to the best mode contemplated at this time for carrying out the invention.

DESCRIPTION OF THE PREFERRED EMBODIMENT

Figure 1:
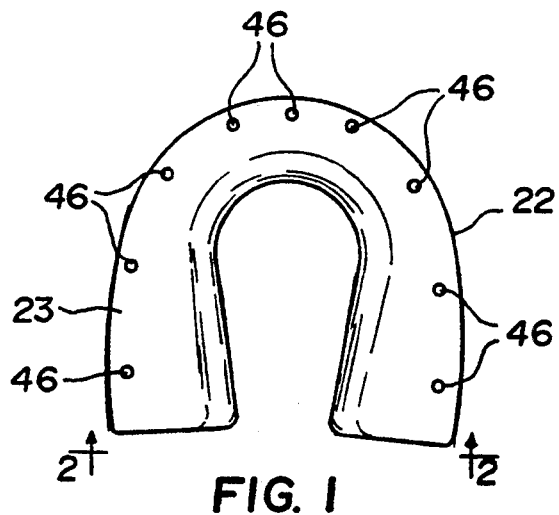
FIG. 1 is a top plan view of a first embodiment of bite registration device embodying principles of the invention.
Figure 4:
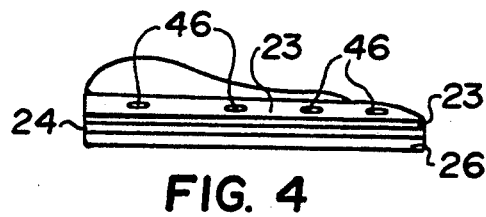
FIG. 4 is a side view of the device taken in the direction of arrows 4—4 in FIG. 2.
Figure 2:
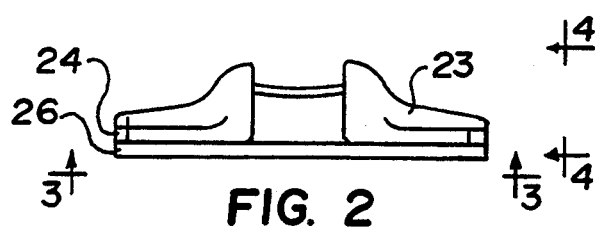
FIG. 2 is a rear view of the device taken in the direction of arrows 2—2 in FIG. 1.
Figure 3:
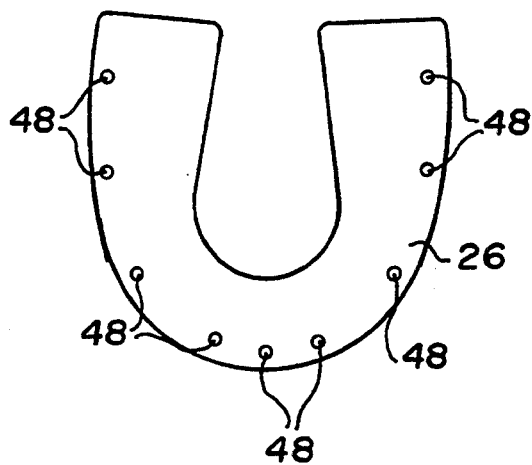
FIG. 3 is a bottom plan view of the device taken in the direction of arrows 3—3 in FIG. 2.
Figure 5:
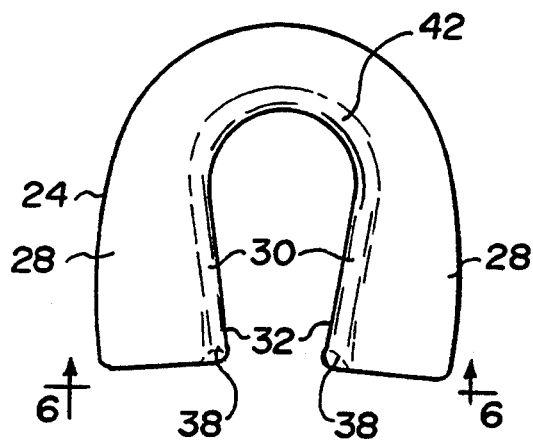
FIG. 5 is a top plan view of one lamina of the device of FIG. 1 by itself.

FIGS. 1–8 relate to a first embodiment of bite registration device 22 embodying principles of the invention. Device 22 comprises three lamina, 23, 24, and 26. Lamina 23 is an upper lamina for confronting an upper dental arch, lamina 26 is a lower lamina for confronting a lower dental arch, and lamina 24, which is shown by itself in FIGS. 5–8, is an intermediate lamina with which both lamina 23 and 26 join.

Looking first at FIGS. 5–8, one will see that lamina 24 comprises a generally flat occlusal wall 28 and an upstanding lingual wall 30. Occlusal wall 28 has a general U-shape for conforming to the general U-shape of the dental arches. It also has a generally uniform thickness throughout. Lingual wall 30 is joined with the lingual margin of occlusal wall 28 throughout the latter's full length around the inside of the U. Together the two walls 28, 30 present a lingual surface 32 that is essentially at a right angle to upper and lower surfaces, 34 and 36 respectively, of wall 28.

Figure 8:
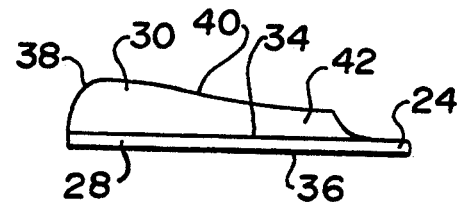
FIG. 8 is a side view of the lamina taken in the direction of arrows 8—8 in FIG. 6.
Figure 6:
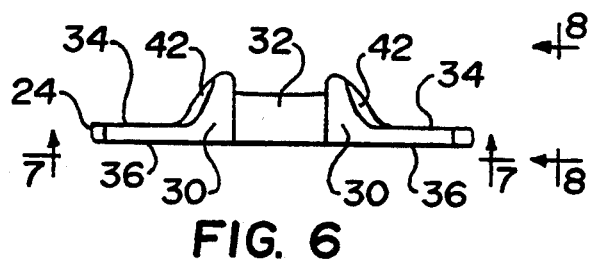
FIG. 6 is a rear view of the lamina taken in the direction of arrows 6—6 in FIG. 5.
Figure 7:
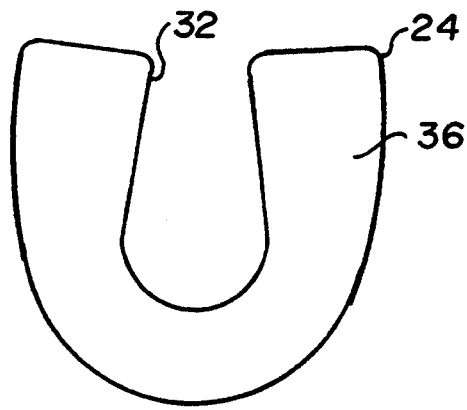
FIG. 7 is a bottom plan view of the lamina taken in the direction of arrows 7—7 in FIG. 6.

Lingual wall 28 extends toward the upper dental arch and is highest proximate the distal ends of the lamina. The upper edges of the distal portions of wall 28 are rounded at 38, and mesial of 38 it slopes gently downward at 40, as best seen in FIG. 8. Wall 28 has a generally labially facing surface 42 that is sloped relative to surface 34, as shown in FIGS. 6 and 8.

Figure 12:
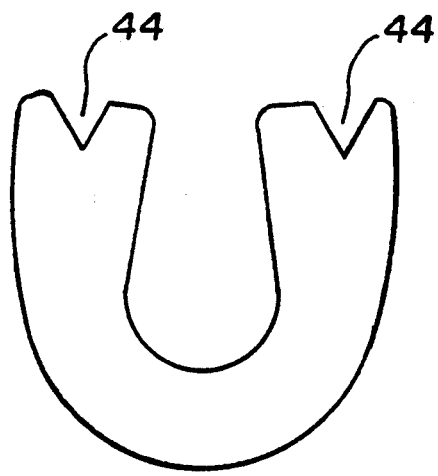
FIG. 12 is a view similar to FIG. 7 showing a modified form.

Lamina 24 is ethylene vinyl acetate that has been injection-molded to the illustrated shape. It has a durometer that is higher than those of lamina 23 and 26, preferably a durometer of at least about 87. As is conventional for measurement of the durometer of ethylene vinyl acetate, durometer measurements are A-scale measurements. Durometers of 97, 95, 92, 90, and 87 are quite well suited for lamina 24. The thickness of occlusal wall 28 is intended to prevent bite-through, and a thickness in the range of 0.071 inch to 0.074 inch is quite well suited for this particular embodiment, although it should be appreciated that such thickness is only exemplary in this embodiment. While FIGS. 5–8 show that the distal ends of lamina 24 extend straight between lingual and labial surfaces, FIG. 12 shows a modified form wherein V-shaped notches 44 are cut into the distal ends. These notches are beneficial in the fabrication of device 22, which will now be explained.

Lamina 23 and 26 are fabricated by injection molding onto lamina 24. The already fabricated lamina 24 is placed in a suitably shaped cavity of an injection mold, and held therein by suitable means which includes a series of stand-off pins. Material for forming lamina 23 and 26 is injected into the cavity so as to cover surfaces 34, 36, and 42 and form to the final shape illustrated by FIGS. 1–4. The stand-off pins are arranged to bear against surfaces 34 and 36 at various locations around the labial margin of occlusal wall 28. Since the stand-off pins are in effect clamping against opposite sides of occlusal wall 28, the injected material must flow around the stand-off pins. After the injected material has cured sufficiently to allow the mold cavity to be opened, and the stand-off pins have been withdrawn, the finished device 22 is left with a series of small holes where the stand-off pins had previously been. In lamina 23, these holes are designated 46, and in lamina 26, they are designated 48. Holes 46, 48 are disposed sufficiently labially that they are labial of the areas where the arch impressions are taken in lamina 23, 26. The pattern of one series of holes 46 matches the pattern of the other series of holes 48, and the holes 46, 48 are all of the same diameter.

A preferred material for lamina 23, 26 is ethylene vinyl acetate that has a durometer no higher than about 40. This material has a characteristic that allows it to bend directly to lamina 24 without the use of any separate intervening adhesive when injection molded onto lamina 24. A further characteristic of this material is that in the finished device 22, lamina 23, 26 are capable of taking very satisfactory impressions of the respective dental arches.

Lamina 26 is a flat, generally uniform thickness, layer that covers the entirety of surface 36, except where the stand-off pins were used to create holes 48. Lamina 23 is in covering relation to the entirety of surface 34, except where the stand-off pins were used to create holes 46. Lamina 23 is also in covering relation to the entirety of surface 42.

After device 22 has been fabricated, it is hermetically sealed, such as in a clear plastic enclosure, and shipped to a dentist or orthodontist for use. The enclosure is opened only at time of use. For use, the device is heated to soften lamina 23, 26 slightly so that they will be ready for taking the impressions of the arches. The device is then promptly placed in the mouth between the arches, and the individual is instructed to bite into it. The softened lamina 23, 26 take the bite impression of the arches. The bite is maintained for a certain amount of time as the device cools to a point where the impressions will not distort when the device is removed. While the conditions for softening the lamina 23, 26 and the time for which the bite is maintained will to some extent depend upon the specific materials and their thicknesses, a device in which the lamina have respective thicknesses of substantially 0.100 inch each and are of 40 durometer ethylene vinyl acetate may be placed in water that is at about 165° F. for about two minutes and fifteen seconds to sufficiently soften the lamina without excessively heating the device. The temperature of the device should not be so hot as to damage tissue when placed intra-orally. It is possible for the mouth to be pre-cooled before device placement and/or during the bite. For this example, the bite should be maintained for about forty-five seconds.

After this maintenance period which provides an initial quenching of the softened device to a condition that will not distort the impressions upon removal of the device from the mouth, the individual is instructed to open the arches. Such degree of care should be exercised at this time because it is likely that the device will have a tendency to remain on one of the arches. In the usual case where the device remains on the upper arch after the arches have been opened, peeling of the device from the upper arch by simultaneously peeling from both distal ends toward the mesial plane has been found to be a satisfactory way to remove the device. Such removal may be facilitated by the dentist or orthodontist using an air syringe to assist in separating the device from the arch.

Figure 9:
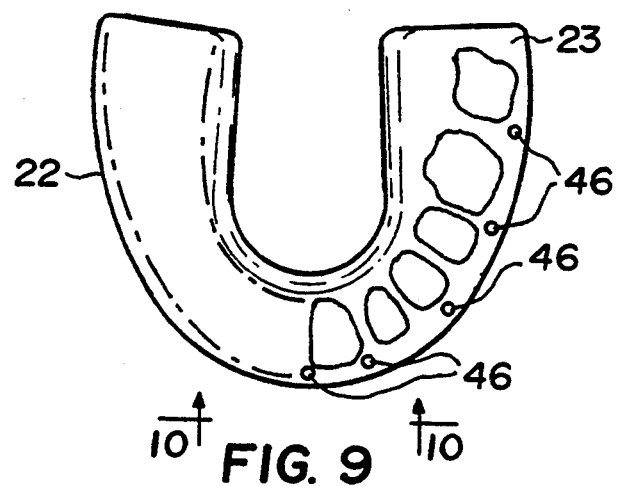
FIG. 9 is a top plan view of the device after use.
Figure 10:
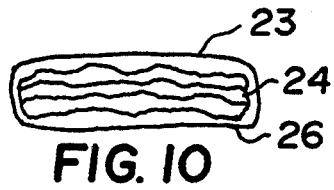
FIG. 10 is a fragmentary view in the direction of arrows 10—10 in FIG. 9.
Figure 11:
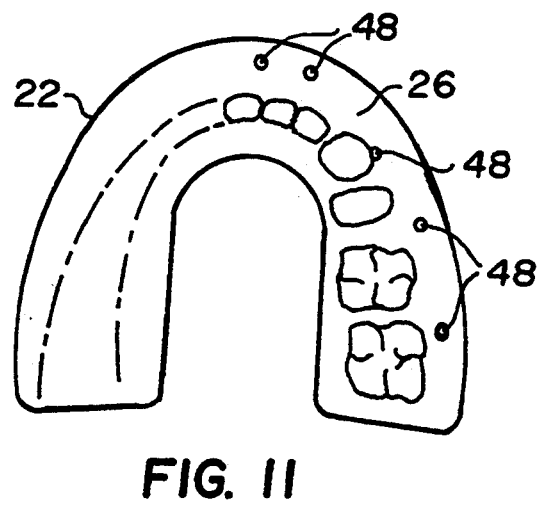
FIG. 11 is a bottom plan view of the device after use.

After it has fully cooled, device 22 exhibits an appearance like that shown by FIGS. 9–11. Upper lamina 23 contains an impression of the upper arch while lower lamina 26 contains an impression of the lower arch. The thicknesses of the lamina are such that the entire occlusal surfaces of the teeth in both arches are impressed to a depth of about the distal one-third of the teeth's crowns. In the specific embodiment that has been described, the total thickness of the occlusal wall is nominally slightly greater than one-quarter inch. If this is deemed too thick for some bite registrations, the thickness may be reduced somewhat so that a closer bite may be obtained. Another embodiment that will be hereinafter described in detail has a significantly smaller thickness for its occlusal wall.

From FIGS. 9 and 11 one can see that holes 46 and 48 remain labial of the impressions although some distortion of the holes' shapes may occur as a result of the impressions. FIG. 10 shows that some wrinkling also occurs as a result of the impressions. There is however no bite-through. The device remains dimensionally stable so long as it is not exposed to heat that would bring lamina 23, 26 to softening temperature; yet the nature of the molded ethylene vinyl acetate provides the device with a certain resilient flexibility. This attribute is very useful when the device is removed free the individual and when it is applied to and removed from a dental arch cast, especially when such application and removal are repeatedly done. The device will not be damaged if accidentally dropped. It is indeed superior to a wax bite registration in many ways.

Figure 13:
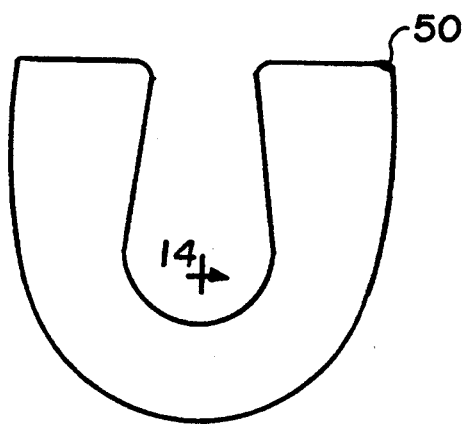
FIG. 13 is a top plan view of a second embodiment of bite registration device embodying principles of the invention.
Figure 14:
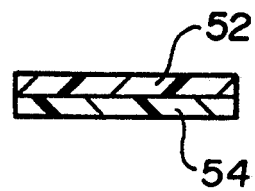
FIG. 14 is an enlarged transverse cross-sectional view in the direction of arrows 14—14 in FIG. 13

FIGS. 13 and 14 illustrate a second embodiment of bite registration device 50. Device 50 is only a two lamina device, unlike the three lamina device 22. Device 50 comprises an upper lamina 52 for confronting an upper dental arch and a lower lamina 54 for confronting a lower dental arch. Each lamina is essentially flat and of uniform thickness throughout. The device is fabricated by creating one lena, such as by injection molding, and then injection molding the other lamina onto it. The result is a generally U-shaped device that has a substantially uniform thickness throughout.

Device 50 is essentially just an occlusal wall since it has no lingual wall like wall 30 of device 22. Device 50 is also considerably thinner than the occlusal wall of device 22. The thickness of device 50 is no greater than 0.100 inch. Such thinness is obtained because of particular materials used. Specifically, lamina 52 which confronts the upper arch is ethylene vinyl acetate that has a durometer no greater than about 73, and lamina 54 which confronts the lower arch is ethylene vinyl acetate that has a durometer of about 90 or about 87. Using two different durometer materials for the two lamina 52, 54, such as those specifically identified, allows lamina 52 to have a thickness in the range from about 0.040 inch to about 0.055 inch and lamina 54 to have a thickness in the range from about 0.020 inch to about 0.045 inch.

Figure 16:
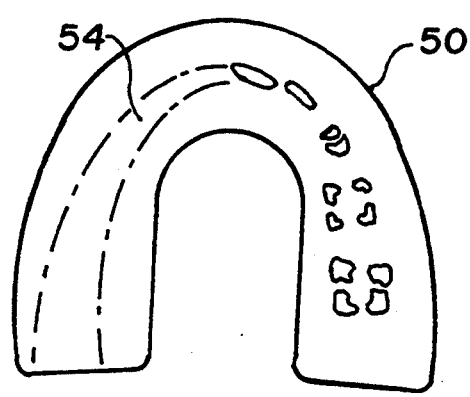
FIG. 16 is a bottom plan view of the device of FIG. 15 after the bite registration has been taken.
Figure 18:
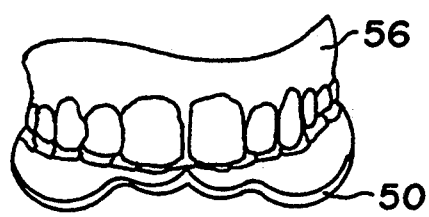
FIG. 18 is a front view of the device as shown in FIG. 17, and showing the device applied to a dental arch cast.
Figure 17:
FIG. 17 is a view in the direction of arrows 17—17 in FIG. 15.

A device 50 constructed with a total occlusal wall thickness of about 0.100 inch exhibits the following characteristics when a bite registration is taken. Lamina 52 will take an impression of the teeth of the upper arch that is much deeper than the impression that lamina 54 takes of the teeth of the lower arch. In fact lamina 54 takes an impression of only tips and cusps of teeth of the lower arch. This is shown in FIG. 16. Lamina 52 takes an impression of the entire occlusal surfaces of the teeth of the upper arch, including a fraction of the distal ends of the teeth's crowns, possibly up to as much as about one-third of the distal ends of the teeth's crowns. Because it is thinner than the occlusal wall of device 22, device 50 experiences more noticeable wrinkling, as shown by FIGS. 17 and 18. This wrinkling in no way impairs the effectiveness of device 50 for its intended purpose, and the fact that the device is thin allows lamina 52 to take sufficiently deep impressions of the upper arch because lamina 54 will deform with it simultaneous with also taking the cusp and tip impression of the lower arch. The bite impressions my experience a small amount of localized bite-through which are not deemed objectionable.

Figure 15:
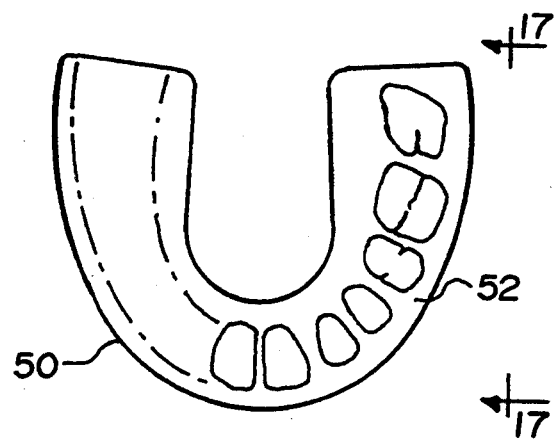
FIG. 15 is a view in the same direction as that of FIG. 13 illustrating the device after a bite registration has been taken.

Device 50 is prepared for use in essentially the same manner as device 22. Because it is thinner, it is not heated quite as long. It is applied to and removed from an individual in the same manner as described for device 22. FIG. 18 shows the fit of device 50 to a dental cast 56. FIG. 15 shows the upper arch impression in device 50. Because it is thinner than the occlusal wall of device 22, device 50 my be somewhat easier to apply to and remove from a dental arch cast. Like device 22, device 50 possesses a certain beneficial flexibility without loss of dimensional stability, assuming of course that it is not exposed to heat that would soften impressions once a bite registration has been taken. It should be noted that the ability to re-soften the impression-taking material may be advantageous if the dentist or doctor is dissatisfied with an initial bite registration. A device may be re-used for a particular patient by re-softening it. Because of health considerations it should be apparent that a given device should not be reused with different individuals.

Figure 19:
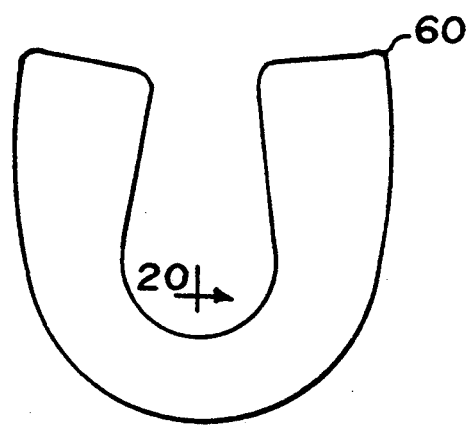
FIG. 19 is a top plan view of a third embodiment of bite registration device embodying principles of the invention.
Figure 20:
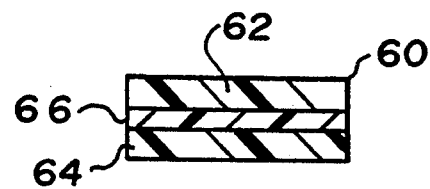
FIG. 20 is an enlarged transverse cross-sectional view in the direction of arrows 20—20 in FIG. 19.

FIGS. 19 and 20 show a third embodiment of device 60 which is like device 22, but without a lingual wall 30. Device 60 is a three lamina device comprising an upper lamina 62, a lower lamina 64, and an intermediate lamina 66. Each of the three lamina is essentially flat and of uniform thickness throughout. Lamina 62, 64 are injection molded onto lamina 66 in similar manner to the injection molding of lamina 23, 26 onto lamina 24. The intermediate lamina 66 could have the V-shaped notches 44, which serve to facilitate the flow of material being injected onto the opposite sides of lamina 66 as the material enters the mold cavity at one of the distal ends of lamina 66 and flows around the U to the opposite distal end. Lacking a lingual wall like wall 30, device 60 may be also held around the lingual margin by stand-off pins during the time that material is being injected onto it to form lamina 62, 64. These stand-off pins would leave series of small holes in analogous fashion to holes 46, 48, but lingually of the impressions. Thickness- and material-wise, lamina 62, 64, 66 may be fabricated in the same way as the corresponding lamina in device 22.

Figure 21:
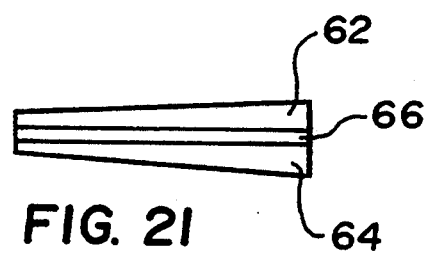
FIG. 21 is a side view showing a modified form.

Bite registration devices embodying principles of the invention are well-suited for taking standard bite registrations. A centric bite registration is perhaps the most common. If a device is used to take a protrusive bite registration, it may be desirable to make the device progressively thicker in the direction from mesial to distal, as shown on a perhaps somewhat exaggerated scale in FIG. 21 for a modified form of device 60 wherein lamina 62 and 64 have such progressively increasing thicknesses while the thickness of lamina 66 is uniform.

The foregoing has disclosed a new and useful bite registration device in several different embodiments. While a presently preferred embodiment has been disclosed, it should be appreciated that certain variations may be made that are within the scope of the following claims.

What is claimed is:

1. A dental arch bite registration device comprising a multi-laminar occlusal wall for placement between a pair of dental arches before they are impressed into the device, one lamina of said occlusal wall adapted to confront one of said pair of dental arches and another lamina of said occlusal wall adapted to confront the other of said pair of dental arches, wherein said one lamina has a durometer different from that of said another lamina such that when said dental arches are impressed into the device during a bite, said one lamina takes an impression of said one arch that is noticeably deeper than the impression that said another lamina takes of said other arch, and wherein the thickness of said occlusal wall is throughout no greater than 0.100 inch before said arches are impressed into the device.

2. A dental arch bite registration device as set forth in claim 1 wherein said one lamina and said another lamina are ethylene vinyl acetate and are directly bonded together without the use of intervening adhesive such that said device has only two lamina.

3. A dental arch bite registration device as set forth in claim 2 wherein said one lamina has a durometer no greater than about 73 and said another lamina has a durometer no lower than about 87.

4. A dental arch bite registration device as set forth in claim 3 wherein said one lamina has a thickness in the range of about 0.020 inch to about 0.045 inch, and said another lamina has a thickness in the range of about 0.040 inch to about 0.055 inch.

5. A dental arch bite registration device as set forth in claim 1 wherein said device takes an impression of about the one-third distal end of teeth of said one arch, and said another lamina takes an impression of only tips and cusps of teeth of said other arch.

6. A dental arch bite registration device as set forth in claim 1 wherein said occlusal wall has a substantially uniform thickness throughout, and each of said one and said another lamina also has a substantially uniform thickness throughout.

7. A dental arch bite registration device comprising a multi-laminar occlusal wall for placement between a pair of dental arches before they are impressed into the device, one lamina of said occlusal wall adapted to confront one of said pair of dental arches and another lamina of said occlusal wall adapted to confront the other of said pair of dental arches, wherein both lamina are toothed-impressionable plastic for taking impressions that are deep enough to include the tips and cusps of teeth of both arches but less than full tooth crowns for obtaining a bite registration, said one lamina has a durometer different from that of said another lamina such that when said dental arches are impressed into the device during a bite, said one lamina takes an impression of said one arch that is noticeably deeper than the impression that said another lamina takes of said other arch, wherein said one lamina and said another lamina are directly bonded together without any intervening lamina between them.

8. A dental arch bite registration device as set forth in claim 7 wherein said one lamina and said another lamina are directly bonded together without the use of intervening adhesive.

9. A dental arch bite registration device as set forth in claim 8 wherein said one lamina and said another lamina are ethylene vinyl acetate, and the thickness of said occlusal wall is throughout no greater than 0.100 inch before said arches are impressed into the device.

10. A dental arch bite registration device comprising a multi-laminar occlusal wall for placement between a pair of dental arches before they are impressed into the device, one lamina of said occlusal wall adapted to confront one of said pair of dental arches and said another lamina of said occlusal wall adapted to confront the other of said pair of dental arches, wherein said one and said another lamina have durometers such that when said dental arches are impressed into the device during a bite, said one lamina takes an impression of said one arch and said another lamina takes an impression of said another arch, and wherein at least one of said one and said another lamina is ethylene vinyl acetate that has a durometer no greater than about 40.

11. A dental arch bite registration device as set forth in claim 10 wherein both said one and said another lamina are ethylene vinyl acetate having durometers no greater than about 40, and wherein both said one lamina and said another lamina are directly bonded to a further lamina that is disposed between them and that has a durometer greater than their durometers, such direct bonding being without the use of separate intervening adhesive.

12. A dental arch bite registration device as set forth in claim 11 wherein said further lamina is also ethylene vinyl acetate and has a durometer of at least about 87.

13. A dental arch bite registration device as set forth in claim 10 wherein said at least one of said one and said another lamina comprises a series of small holes disposed such that when the corresponding arch is impressed therein, said holes are disposed labially of the corresponding arch.

14. A dental arch bite registration device as set forth in claim 10 wherein a further lamina is disposed between said one and said another lamina, said further lamina comprises a lingual wall, and said at least one lamina covers at least a portion of said lingual wall.

15. A dental arch bite registration device as set forth in claim 10 wherein a further lamina is disposed between said one and said another lamina, said further lamina is an injection-molded part that is fabricated prior to the association of said one and said another lamina with said further lamina, and said further lamina comprises a notch at at least one of its distal ends.

16. A dental arch bite registration device comprising a multi-laminar occlusal wall, each lamina formed of an impression material for placement between a pair of dental arches before they are impressed into the device, one lamina of said occlusal wall adapted to confront one of said pair of dental arches and another lamina adapted to confront the other of said pair of dental arches such that when said dental arches are impressed into the device, said one lamina takes an impression of said one arch and said another lamina takes an impression of said other arch, wherein said one lamina comprises a series of small holes that are located about the periphery of said occlusal wall and adjacent an area adapted to receive an impression.

17. A dental arch bit registration device as set forth in claim 16 wherein said series of small holes are disposed labially of said area.

18. A dental arch bite registration device as set forth in claim 16 wherein said series of small holes extend completely through said one lamina.

19. A dental arch bite registration device comprising a multi-laminar U-shaped disk that is generally entirely flat between labial and lingual margins, one lamina of said disk being a tooth-impressionable plastic adapted to confront one of a pair of dental arches and another lamina of said disk being a tooth-impressionable plastic adapted to confront the other of said pair of dental arches such that when said disk is placed between said arches and they are impressed into said disk, said one lamina takes an impression of said one arch and said another lamina takes an impression of said other arch, wherein said one and said another lamina are joined via an intermediate lamina that is also a tooth-impressionable plastic of a durometer different from the durometers of said one and said another lamina.

20. A dental arch bite registration device as set forth in claim 19 wherein said disk has a thickness that is thicker at its distal ends than at the mesial plane.

* * * * *